US011737898B2

(12) United States Patent
Gloss et al.

(10) Patent No.: US 11,737,898 B2
(45) Date of Patent: Aug. 29, 2023

(54) TENSION MEMBER ROUTING DESIGNS TO ACHIEVE TRANSCATHETER STENTED PROSTHESIS COMPRESSION

(71) Applicant: Medtronic, Inc., Minneapolis, MN (US)

(72) Inventors: Michael Gloss, Minneapolis, MN (US); Patrick Griffin, Galway (IE); Jeffrey Sandstrom, Scandia, MN (US); David O'Toole, Galway (IE); Rishi Manda, Stillwater, MN (US); Niall Duffy, Ballybrit (IE)

(73) Assignee: MEDTRONIC, INC., Minneapolis, MN (US)

( * ) Notice: Subject to any disclaimer, the term of this patent is extended or adjusted under 35 U.S.C. 154(b) by 328 days.

(21) Appl. No.: 16/995,351

(22) Filed: Aug. 17, 2020

(65) Prior Publication Data

US 2020/0375770 A1    Dec. 3, 2020

Related U.S. Application Data

(62) Division of application No. 15/938,576, filed on Mar. 28, 2018, now Pat. No. 10,772,749.

(Continued)

(51) Int. Cl.
*A61F 2/95* (2013.01)
*A61F 2/24* (2006.01)
*A61F 2/966* (2013.01)

(52) U.S. Cl.
CPC ............... *A61F 2/95* (2013.01); *A61F 2/243* (2013.01); *A61F 2/2439* (2013.01);
(Continued)

(58) Field of Classification Search
CPC .......... A61F 2/95; A61F 2/243; A61F 2/2439; A61F 2/9522; A61F 2002/9511;
(Continued)

(56) References Cited

U.S. PATENT DOCUMENTS 5,776,186 A * 7/1998 Uflacker ................. A61F 2/966
606/195
9,216,018 B2   12/2015 Sutherland et al.
(Continued)

OTHER PUBLICATIONS

PCT/US2018/024937, The International Search Report and The Written Opinion, dated Jul. 10, 2018, 13 pages.

*Primary Examiner* — Timothy J Neal
*Assistant Examiner* — Andrew P. Restaino
(74) *Attorney, Agent, or Firm* — Wentsler LLC

(57) ABSTRACT

The present disclosure relates to delivery devices for transcatheter stented prosthesis loading, delivery and implantation. The delivery devices provide a loaded delivery state in which the stented prosthesis is loaded and compressed over the delivery device. The compression of the stented prosthesis can be adjusted with one or more elongate tension members, which extend around the stented prosthesis and proximately to an actuation and release assembly that can be provided as part of a handle assembly. The delivery device can be manipulated to adjust tension in the tension members to permit the stented prosthesis to compress, self-expand, and ultimately release from the shaft assembly. In some embodiments, the tension in one or more tension members is adjusted with one or more actuation and release assemblies.

6 Claims, 15 Drawing Sheets

Related U.S. Application Data

(60) Provisional application No. 62/477,516, filed on Mar. 28, 2017.

(52) U.S. Cl.
CPC ..... *A61F 2/9522* (2020.05); *A61F 2002/9511* (2013.01); *A61F 2002/9665* (2013.01)

(58) Field of Classification Search
CPC ..... A61F 2002/9665; A61B 2017/1132; A61B 17/1146; A61B 2017/1107; A61B 2017/1103
See application file for complete search history.

(56) References Cited

U.S. PATENT DOCUMENTS

| | | | |
|---|---|---|---|
| 2004/0116996 A1* | 6/2004 | Freitag | A61F 2/95 623/1.11 |
| 2007/0016281 A1 | 1/2007 | Melsheimer | |
| 2007/0100427 A1 | 5/2007 | Perous | |
| 2007/0233223 A1 | 10/2007 | Styrc | |
| 2011/0218622 A1 | 9/2011 | Shaolian et al. | |
| 2012/0053671 A1 | 3/2012 | McHugo et al. | |
| 2013/0261726 A1* | 10/2013 | Alger | A61F 2/958 623/1.11 |
| 2013/0289713 A1 | 10/2013 | Pearson et al. | |
| 2016/0199207 A1* | 7/2016 | Treacy | A61F 2/82 623/1.12 |
| 2016/0250051 A1 | 9/2016 | Lim et al. | |
| 2017/0165067 A1 | 6/2017 | Barajas-Torres et al. | |

\* cited by examiner

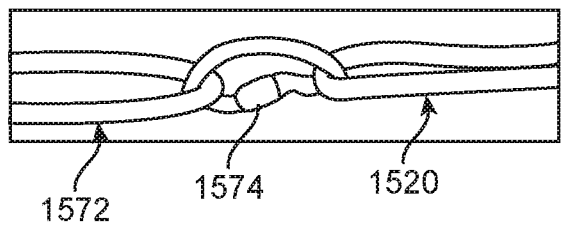
FIG. 21
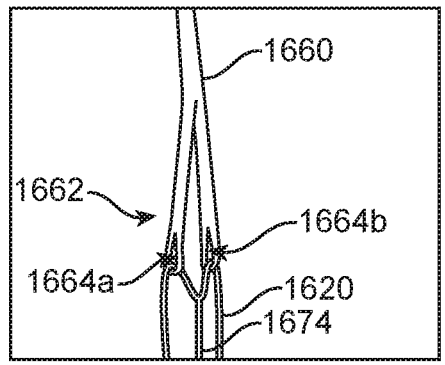
FIG. 22
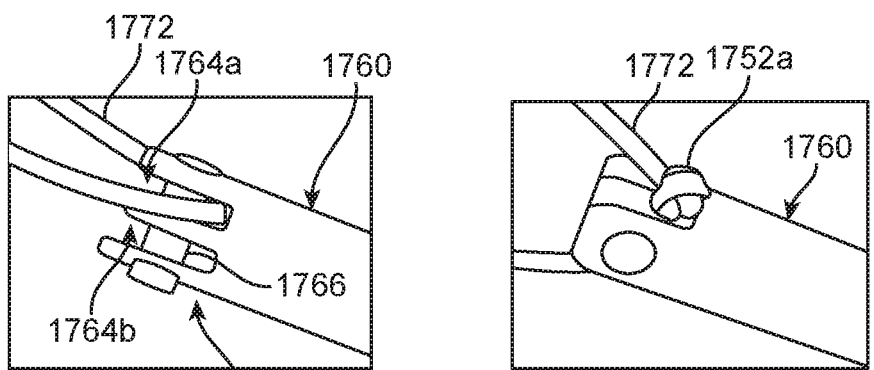
FIG. 23A
FIG. 23B
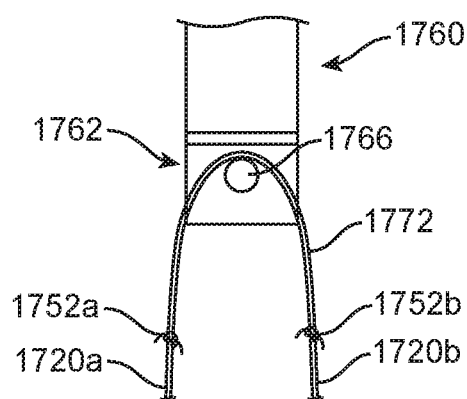
FIG. 23C

TENSION MEMBER ROUTING DESIGNS TO ACHIEVE TRANSCATHETER STENTED PROSTHESIS COMPRESSION

CROSS-REFERENCE TO RELATED APPLICATIONS

This application is a Divisional application of Ser. No. 15/938,576, filed on Mar. 28, 2018, entitled "TENSION MEMBER ROUTING DESIGNS TO ACHIEVE TRANSCATHETER STENTED PROSTHESIS COMPRESSION," now allowed, which claims the benefit of the filing date of U.S. Provisional Patent Application Ser. No. 62/477,516, filed Mar. 28, 2017, entitled "TENSION MEMBER ROUTING DESIGNS TO ACHIEVE TRANSCATHETER STENTED PROSTHESIS COMPRESSION," the entire teachings of which are incorporated herein by reference.

BACKGROUND

This disclosure relates to delivery devices and components for a transcatheter stented prosthesis, such as a stented prosthetic heart valve.

A human heart includes four heart valves that determine the pathway of blood flow through the heart: the mitral valve, the tricuspid valve, the aortic valve, and the pulmonary valve. The mitral and tricuspid valves are atrio-ventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Diseased or otherwise deficient heart valves can be repaired or replaced using a variety of different types of heart valve surgeries. One conventional technique involves an open-heart surgical approach that is conducted under general anesthesia, during which the heart is stopped and blood flow is controlled by a heart-lung bypass machine.

More recently, minimally invasive approaches have been developed to facilitate catheter-based implantation of the valve prosthesis on the beating heart, intending to obviate the need for the use of classical sternotomy and cardiopulmonary bypass. In general terms, an expandable valve prosthesis is compressed about or within a catheter, inserted inside a body lumen of the patient, such as the femoral artery, and delivered to a desired location in the heart where the valve prosthesis is then deployed.

The disclosure presents improvements related to the above.

SUMMARY

The present disclosure relates to delivery devices for transcatheter stented prosthesis loading, delivery and implantation. Such delivery devices can include, for example, an optional outer delivery sheath assembly, a shaft assembly and a handle assembly. The delivery devices provide a loaded delivery state in which the stented prosthesis is loaded and compressed over the shaft assembly. Compression of the stented prosthesis can be adjusted with one or more elongate tension members, which extend around the stented prosthesis and proximately to an actuation and release assembly, which can, in some embodiments, be provided in the handle assembly. The delivery device can be manipulated to adjust tension in the tension members to permit the stented prosthesis to compress, self-expand, and ultimately release from the shaft assembly.

Various disclosed embodiments can include one or more balancing elements or are otherwise configured to distribute the tension applied to the tension members to provide even crimping and expansion of the stented prosthesis. In embodiments where only one tension member is provided, various disclosed balancing elements can distribute the tension applied along a length of the tension member. In certain embodiments, the balancing element interconnects the one or more tension members to an actuator that can be withdrawn proximally to tension one or more tension members. The balancing element defines an aperture formed in or connected to the actuator, for example, in which the at least one tension member can slide. In this way, each tension member will naturally slide as the actuator tensions and adjust the length of tension member positioned around the stented prosthesis so that the tension applied by each balanced tension member to the stented prosthesis is generally equal both between tension members connected to the balancing element and along a length of the tension member if only one tension member is employed to compress multiple areas of the stented prosthesis. In various embodiments, the balancing element is a ring interconnecting a plurality of tension members, wherein the balancing element is separate from the actuator. In further embodiments, multiple balancing elements are provided.

As discussed above, various embodiments include one an actuation and release assembly. The actuation and release assembly can optionally adjust the tension in two or more tension members simultaneously. In other embodiments a plurality of an actuation and release assemblies are provided to either simultaneously or individually actuate a plurality of respective tension members. In such embodiments, one or more balancing elements can be incorporated into the delivery device to balance the tension within one or more tension members as the actuation and release assemblies vary tension in the respective tension members.

BRIEF DESCRIPTION OF THE DRAWINGS

FIG. 21 is a partial, schematic illustration of one balancing element that can be used with the embodiments disclosed herein.

FIG. 22 is a partial, schematic illustration of an alternate balancing element that can be used with the embodiments disclosed herein.

FIG. 23A is a partial, front view of an alternate balancing element that can be used with the embodiments disclosed herein.

FIG. 23B is a partial, side view of the balancing element of FIG. 23B.

FIG. 23C is a partial, schematic, cross-sectional illustration of the balancing element of FIGS. 23A-23B.

DETAILED DESCRIPTION

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. As used herein, with reference to an implanted stented prosthesis, the term "outflow" is understood to mean downstream to the direction of blood flow, and the term "inflow" is understood to mean upstream to the direction of blood flow.

Figure 1:
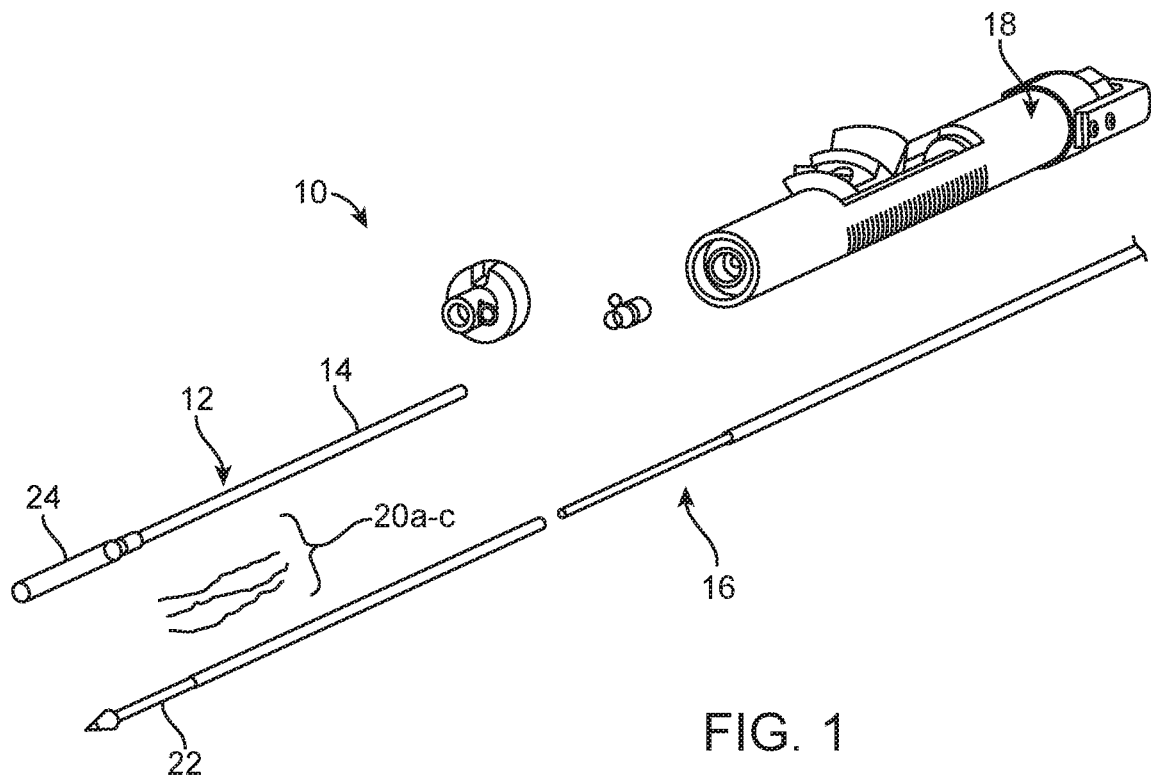
FIG. 1 is a perspective view of an example of a delivery device for delivering a stented prosthesis.
Figure 2A:
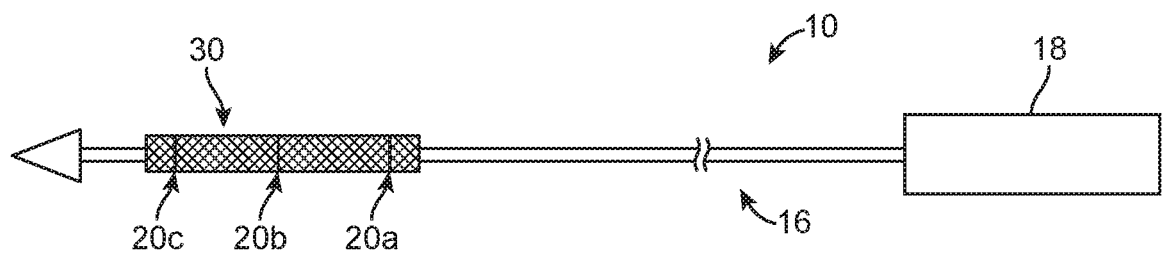
FIG. 2A is a schematic illustration of the delivery device of FIG. 1 having the stented prosthesis positioned over an shaft assembly of the delivery device in a compressed arrangement with a plurality of elongate tension members.
Figure 2B:
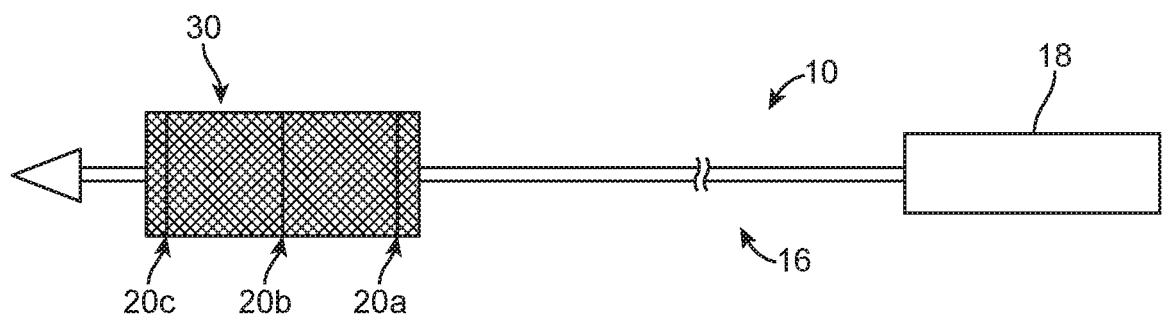
FIG. 2B is a schematic illustration of the delivery device of FIG. 2A having the stented prosthesis positioned over the shaft assembly of the delivery device in an expanded arrangement with the plurality of elongate tension members.

As described below, aspects of the present disclosure relate to transcatheter stented prosthesis delivery devices utilizing one or more elongate tension members (e.g., sutures, cords, wires or filaments) to compressively retain the stented prosthesis on the delivery device during delivery to a target site. By way of background, general components of one non-limiting example of a delivery device 10 with which some embodiments of the present disclosure are useful are illustrated in FIGS. 1-2B. The delivery device 10 is arranged and configured for percutaneously delivering a stented prosthesis 30 (schematically illustrated) to a patient's native defective heart valve or other target site. The delivery device 10 includes an optional outer sheath assembly 12 having an outer sheath 14, a shaft assembly 16 and a handle assembly 18. One or more elongate tension members 20a-c are provided, and can be considered part of the delivery device 10 in some embodiments or as part of the stented prosthesis 30 in other embodiments. The delivery device 10 provides a loaded, compressed arrangement (FIG. 2A) in which the stented prosthesis 30 is loaded over and is compressively retained on a distal portion 22 of the shaft assembly 16 by the tension members 20a-c. As is schematically illustrated in FIGS. 2A-2B, compression of the stented prosthesis 30 is adjustable by varying the tension in the one or more tension members 20a-c. In this embodiment, the outer sheath 14 is interconnected to a capsule 24 that is selectively disposed over the compressed stented prosthesis 30 and assists in constraining the stented prosthesis 30. Once loaded, compressed and optionally sheathed by the capsule 24, the stented prosthesis 30 is delivered to the native defective heart valve. When the stented prosthesis 30 is at the target site, the capsule 24 is withdrawn and tension in the tension members 20a-c is lessened or released to permit the stented prosthesis 30 to self-expand to an expanded arrangement, partially releasing and ultimately fully deploying the stented prosthesis 30 from the shaft assembly 16 (see, FIG. 2B). Movement of the outer sheath 14 and capsule 24 relative to the stented prosthesis 30 can be actuated by the handle assembly 18. As will be discussed in detail below, many of the disclosed embodiments are arranged and configured to distribute and balance the tensioning force applied to one or more tension members 20a-c along a length of the tension member and between two or more tension members.

As referred to herein, stented prostheses useful with the various devices and methods of the present disclosure may assume a wide variety of configurations. Stented prostheses can include, for example, stented prosthetic heart valves ("prosthetic valves"), such as a bioprosthetic heart valve having tissue leaflets or a synthetic heart valve having polymeric, metallic or tissue-engineered leaflets, and can be specifically configured for replacing valves of the human heart. The stented prostheses of the present disclosure may be self-expandable, balloon expandable and/or mechanically expandable or combinations thereof. In general terms, the prosthetic valves of the present disclosure include a stent or stent frame having an internal lumen maintaining a valve structure (tissue or synthetic), with the stent frame having a normal, expanded condition or arrangement and collapsible to a compressed condition or arrangement for loading within the delivery device. For example, the stents or stent frames are support structures that comprise a number of struts or wire segments arranged relative to each other to provide a desired compressibility and strength to the prosthetic valve. The struts or wire segments are arranged such that they are capable of self-transitioning from, or being forced from, a compressed or collapsed arrangement to a normal, radially expanded arrangement. The struts or wire segments can be formed from a shape memory material, such as a nickel titanium alloy (e.g., Nitinol™). The stent frame can be laser-cut from a single piece of material, or can be assembled from a number of discrete components.

Figure 3A:
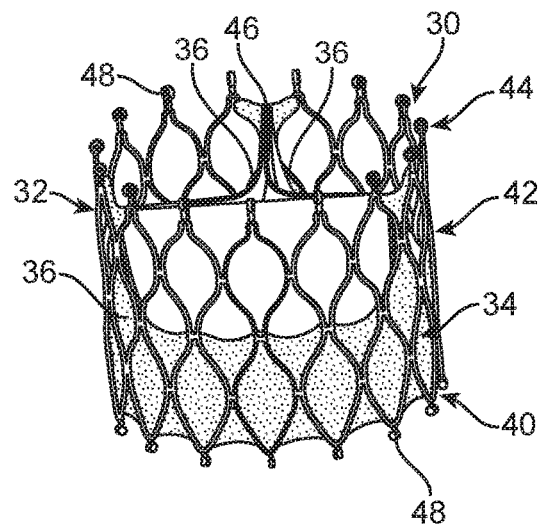
FIG. 3A is a perspective view of one stented prosthesis, a stented prosthetic heart valve, that can be used with the delivery devices disclosed herein shown in the expanded arrangement.
Figure 3B:
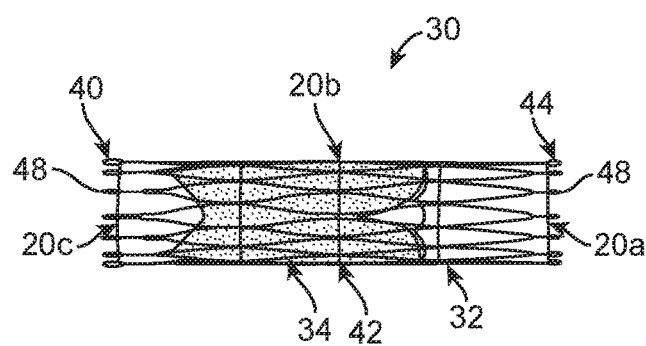
FIG. 3B is a front view of the stented prosthesis of FIG. 3A in the compressed arrangement.

One non-limiting example of the stented prosthesis 30 is illustrated in detail in FIGS. 3A-3B. As a point of reference, the stented prosthesis 30 is shown in a normal or expanded arrangement in the view of FIG. 3A and a compressed arrangement in the view of FIG. 3B. The stented prosthesis 30 shown in this embodiment is a stented prosthetic heart valve and includes a stent or stent frame 32 and a valve structure 34. The stent frame 32 can assume any of the forms mentioned above, and is generally constructed to be self-expandable from the compressed arrangement to the normal, expanded arrangement. As discussed above, compression of the stented prosthesis 30 can be achieved with one or more tension members 20a-c. Three tension members 20a-c are referenced, however, the use of fewer or more tension members is envisioned.

If provided, the valve structure 34 of the stented prosthesis 30 can assume a variety of forms, and can be formed, for example, from one or more biocompatible synthetic materials, synthetic polymers, autograft tissue, homograft tissue, xenograft tissue, or one or more other suitable materials. In some embodiments, the valve structure 34 can be formed, for example, from bovine, porcine, equine, ovine and/or other suitable animal tissues. In some embodiments, the valve structure 34 is formed, for example, from heart valve tissue, pericardium, and/or other suitable tissue. In some embodiments, the valve structure 34 can include or form one or more leaflets 36. For example, the valve structure 34 can be in the form of a tri-leaflet bovine pericardium valve, a bi-leaflet valve, or another suitable valve.

In some prosthetic valve constructions, such as that of FIGS. 3A-3B, the valve structure 34 can comprise two or three leaflets 36 that are fastened together at enlarged lateral end regions to form commissural joints, with the unattached edges forming coaptation edges of the valve structure 34. The leaflets 36 can be fastened to a skirt that in turn is attached to the stent frame 32. The stented prosthesis 30 includes a first end 40 (inflow), an opposing second end 44 (outflow) and an intermediate section or waist 42. As shown, the stent frame 32 can have a lattice or cell-like structure, and optionally forms or provides posts 46 corresponding with commissures of the valve structure 34 as well as features 48 (e.g., crowns, eyelets or other shapes) at the first and second ends 40, 44. If provided, the posts 46 are spaced equally around frame 32 (only one post 46 is clearly visible in FIG. 3A).

Figure 4:
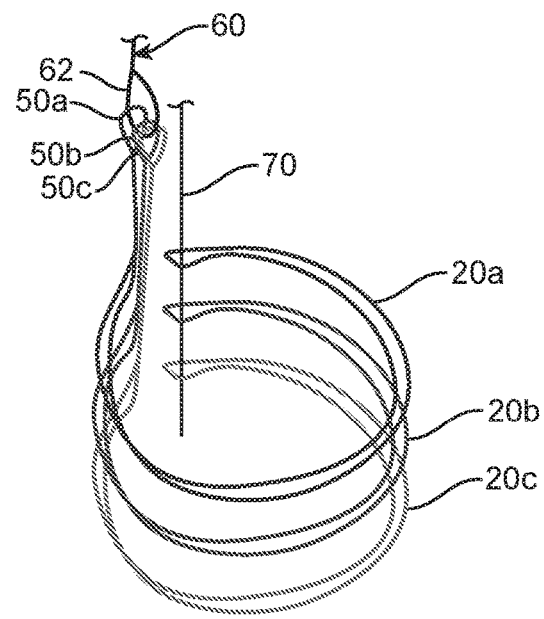
FIG. 4 is a schematic illustration of how three elongate tension members can be releasably positioned around a stented prosthesis with a release pin and tension in the tension members can be adjusted with a single actuator (the stented prosthesis is not shown for ease of illustration).

Referring now also to FIG. 4, which illustrates one way in which the tension members can be positioned or routed around the stented prosthesis (not shown for ease of illustration). This embodiment includes an outflow tension member 20a, waist tension member 20b and an inflow tension member 20c, each of which are wrapped around a release pin 70 and terminate at a respective end 50a-c, which is interconnected to a connector 62 of an actuator 60. The release pin 70 can be provided, for example, within or along the shaft assembly 16 of FIG. 1 or as part of a similar device. In this illustrated embodiment, each end 50a-c is a loop that is connected to the connector 62. Retraction of the actuator 60 proximally when the release pin 70 is engaged with the tension members 20a-c withdraws and tensions the tension members 20a-c. It has been observed that very specific or precise tension member 20a-c lengths are required in order to achieve a uniform crimp of the stented prosthesis. Once the stented prosthesis is deployed, the release pin 70 can be retracted to disengage from the tension members 20a-c so that the tension members 20a-c be fully withdrawn by the actuator 60 to be removed from the patient. It is noted that all embodiments disclosed herein that utilize a release pin can operate in a similar fashion.

Figure 5:
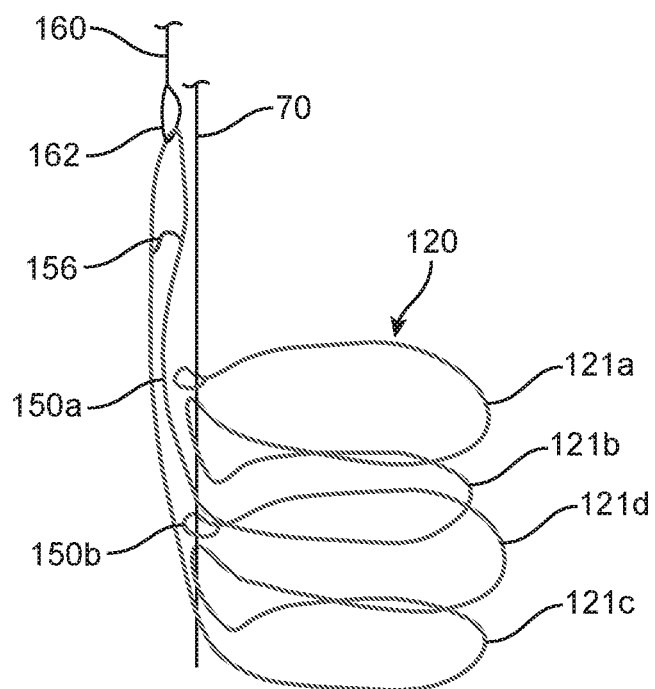
FIG. 5 is a schematic illustration of an alternate way in which a single elongate tension member can be releasably retained around a stented prosthesis (the stented prosthesis is not shown for ease of illustration).

Turning now also to FIG. 5, which illustrates an alternate way in which tension in an elongate tension member 120 can be tensioned with an actuator 160 having a connector 162 to provide crimping of a stent frame of a stented prosthesis (the stented prosthesis is not shown for ease of illustration). In this embodiment, one tension member 120 is provided, the tension member 120 capable of being wrapped around the stent frame four times to create four tension loops 121a-d. The tension member 120 includes two looped ends 150a-b and can be tensioned by proximally retracting the actuator 160. In this embodiment, the connector 162 is a ring or the like at a distal end of the actuator 160. Optionally, the tension member 120 can be configured to limit the length that it can pass or slide within the connector 162. For example, the tension member 120 can include an interconnecting member 156 spanning between opposing sides of the tension member 120, for example.

As one example, the tension member 120 is routed as follows. One looped end 150a of the tension member 120 can be threaded through the release pin 70 and then wrapped around the stent frame back and around the release pin 70 to form a first tension loop 121a. The tension member 120 can then make one more pass around the stent frame to form a second tension loop 121b before being routed up through the connector 162 and then back down to the distal end of the stent frame where the tension member 120 is wrapped again around the stent frame to make a third tension loop 121c. The third tension loop 121c terminates at the release pin 70, where the tension member 120 again wraps around the release pin 70 and then around the stent frame to form a fourth tension loop 121d positioned between the second and third tension loops 121b, 121c. The release pin 70 is then positioned within the second looped end 150b to secure the tension member 120 to the delivery device and the stent frame. Some temporary withdrawing and other maneuvering of the release pin 70 may be required to ultimately obtain the routing configuration of FIG. 5.

Figure 6:
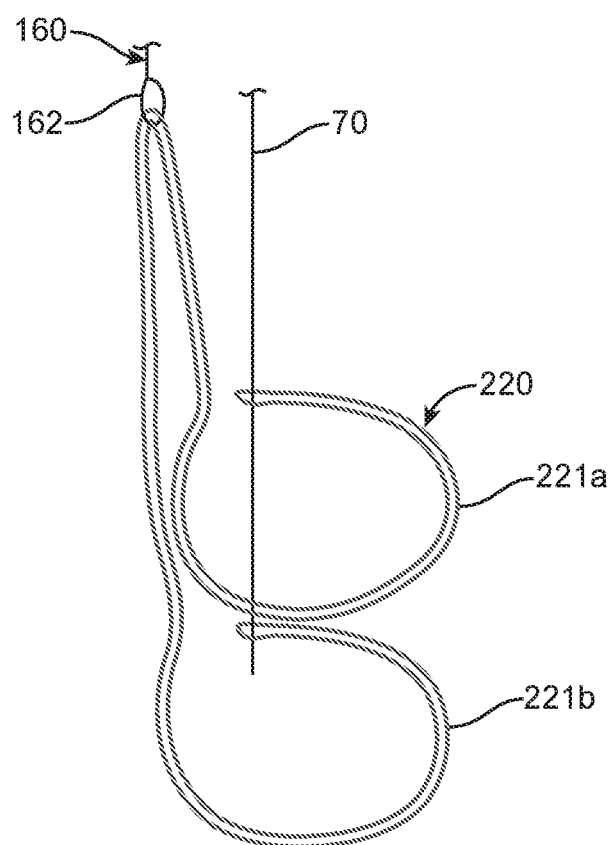
FIG. 6 is a schematic illustration of yet another way in which a single elongate tension member can be releasably retained around a stented prosthesis (the stented prosthesis is not shown for ease of illustration).

Turning now also to FIG. 6, which illustrates the actuator 160 of FIG. 5 used to adjust the tension in a single tension member 220 that is routed to form two tension loops 221a-b, each having a double thickness of tension member material. The tension member 220 is releasably retained around a stent frame of a stented prosthesis (not shown for ease of illustration) with the release pin 70. As with the prior embodiments, movement of the actuator 160 tensions and releases the tension applied by the tension member 220 around the stent frame. In this configuration, the tension member 220 can slide and naturally adjust within the connector 162, thus balancing the tension in each tension loop 221a-b. This configuration is particularly useful for shorter prosthetic valves or stent frames and/or if tighter crimping force is not required.

Figure 7:
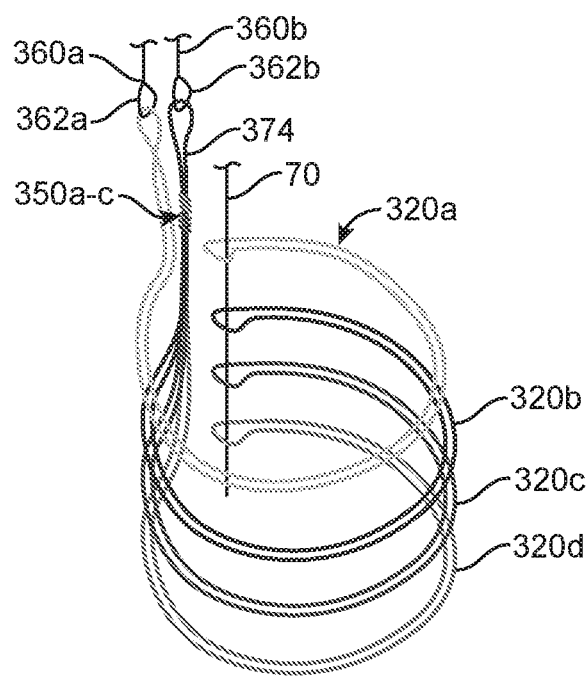
FIG. 7 is a schematic illustration of a way in which multiple elongate tension members can be releasably retained around a stented prosthesis (the stented prosthesis is not shown for ease of illustration).

Turning now also to FIG. 7, which illustrates a configuration including two actuators 360a-b, both of which include respective connectors 362a-b. Each of the actuators 360a-b is interconnected to one or more elongate tension members 320a-d. As with the prior embodiments, proximal/distal movement of the actuator 360a-b can selectively tension and release the tension applied to the respective tension member(s) 320a-d. Each of the tension members 320a-d forms a respective tension loop around a stent frame of a stented prosthesis (not shown for ease of illustration). In one configuration, a first tension member 320a is threaded through one connector 362a, around the stent frame and around the release pin 70, then back to the connector 362a, where two ends of the elongate tension member 320a are tied or otherwise connected so that the tension member 320a forms a continuous loop of material. Three additional elongate tension members 320b-d are routed around the stent frame and release pin 70 in a similar manner but are tied or otherwise connected together distal to the respective connector 362b. The connected ends 350a-c can be jointly connected to an interconnecting member 374, which is a loop slidably retained within the connector 362b. The interconnecting member 374 can be considered part of the tension members 320a-c. By having multiple actuators 360a-b, if one of the actuators 360a-b is rendered nonfunctional, crimping of the stent frame may still be achieved with the other actuator. Additionally, controlled crimping of the stent frame and controlled deployment of the stent frame or prosthetic valve at different levels may be achieved by selectively adjusting the position of each actuator 360a-b.

Figure 8:
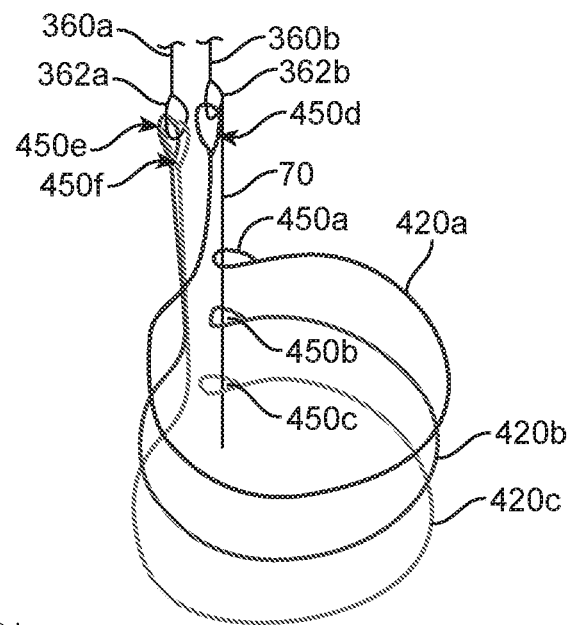
FIG. 8 is a schematic illustration of another way in which multiple elongate tension members can be releasably retained around a stented prosthesis (the stented prosthesis is not shown for ease of illustration).

Now also referring to FIG. 8, which illustrates a configuration that also includes the two actuators 360a-b of FIG. 7. Each of the actuators 360a-b is interconnected to one or more elongate tension members 420a-c. As with the prior embodiments, movement of the actuator 420a-c selectively tensions or releases the tension applied to the respective tension member(s) 420a-c connected thereto. In this embodiment, each tension member 420a-c includes two looped ends 450a-f. One looped end 450a-c of each tension member 420a-c is releasably secured to the release pin 70 and then wrapped around the stent frame (not shown for ease of illustration) and then is movably secured to one of the connectors 362a-b. In this embodiment, the second looped end 450d-f of each tension member 420a-c is connected to one respective connectors 362a-b such that the looped end 450d-f can slide within and with respect to one respective connector 362a-b. In one embodiment, as illustrated, the first actuator 360a is interconnected to and controls the tensioning in two elongate members 420b-c and the second actuator 360b is interconnected to and controls the tension in one elongate member 420a.

Figure 9:
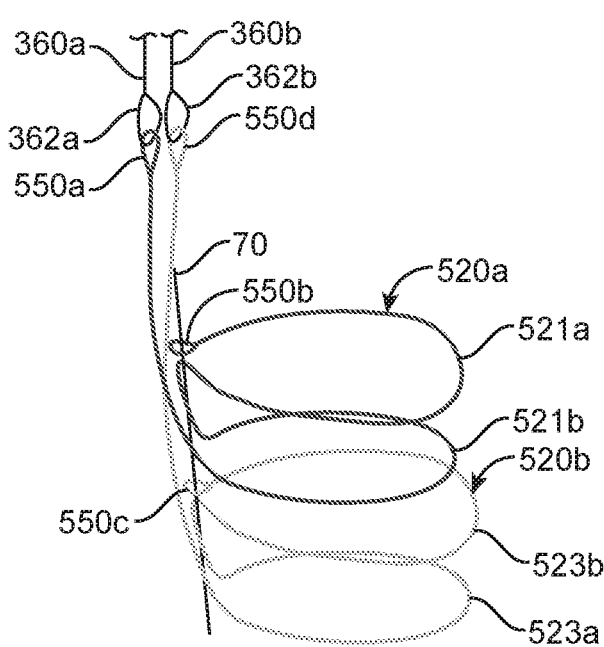
FIG. 9 is a schematic illustration of a way in which two elongate tension members can be releasably retained around a stented prosthesis (the stented prosthesis is not shown for ease of illustration).

Turning now also to FIG. 9, which illustrates an alternate way in which two elongate tension members 520a-b can be routed and connected to the actuators 360a-b of FIGS. 7-8. In this embodiment, the first tension member 520a is wrapped around a stent frame of a stented prosthesis two revolutions to create two spaced-apart tension loops 521a-b and the second tension member 520b being wrapped around the stent frame two revolutions to create two additional spaced-apart tension loops 523a-b (the stent frame is not shown for ease of illustration). The tension members 520a-b each include a looped end 550a, 550d slidably connected with one respective connector 362a-b and can be tensioned with proximal retraction of the respective actuator 360a-b. Secure and release of the tension members 520a, 520b with respect to the stent frame can be accomplished with the release pin 70, as discussed above with respect to prior embodiments, for example.

Figure 10:
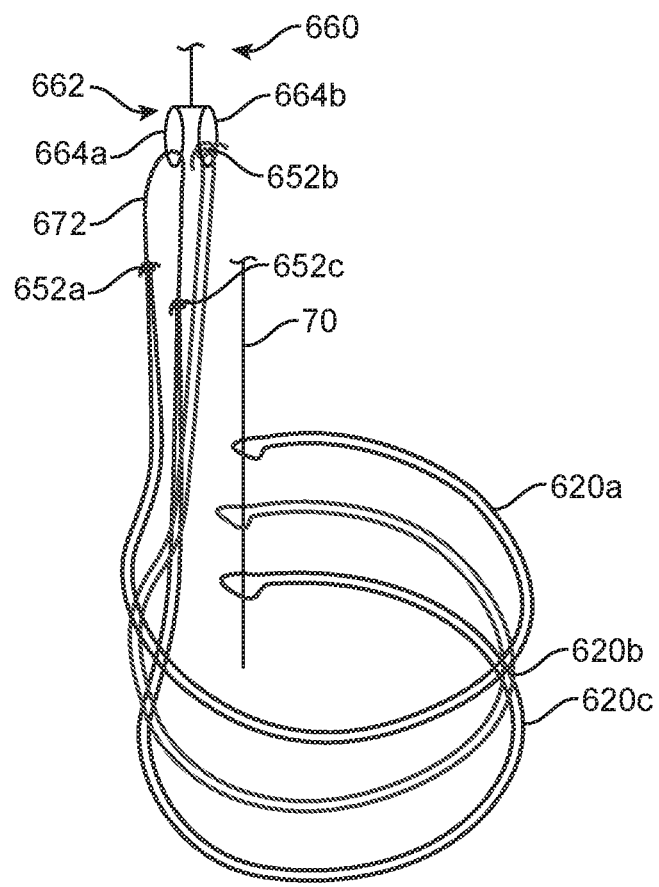
FIG. 10 is a schematic illustration of a way in which a plurality of elongate tension members can be releasably retained around a stented prosthesis (the stented prosthesis is not shown for ease of illustration).

Now also referring to FIG. 10, which illustrates one way in which elongate tension members 620a-c can be configured to be tensioned with an actuator 660 and slide within and with respect to the actuator 660 such that the tension in and between at least two of the tension members (e.g., tension members 620a and 620c) is balanced. In this embodiment, the actuator 660 includes a connector or balancing element 662 having first and second rings 664a-b to balance the tension in the tension members 620a, 620c to provide even crimping of a stent frame of a stented prosthesis at the inflow and outflow ends (the stented prosthesis is not shown for ease of illustration). In this embodiment, three tension members 620a-c are provided. This embodiment includes an outflow tension member 620a, waist tension member 620b and an inflow tension member 620c, each of which are wrapped around a release pin 70 and terminate at a respective end 652a-c, which is directly or indirectly interconnected to one ring 664a-b of the connector 662. The interconnecting member 672 is threaded through the ring 664a to allow the interconnecting member 672 and tension members 620a, 620c to slide and equalize the tension in the outflow and the inflow tension members 620a, 620c applied by the actuator 660. In this illustrated embodiment, the outflow tension member 620a and inflow tension member 620c are tied to an interconnecting member 672 with a knot 652a, 652c. The interconnecting member 672 can be considered part of the tension members 620a, 620c. In some embodiments, the knots 652a, 652c or other retaining elements are sized such that they cannot pass through the ring 664a as the tension members 620a, 620c slide within and adjust with respect to the ring 664a.

The intermediate tension member 620b of this embodiment is not balanced with respect to the other tension members 620a, 620c and is only balanced along its own length via sliding within the second ring 664b. The inventors have observed that compressing a waist of a stented prosthesis generally requires a greater amount of force as compared to the ends, which would overall increase forces on the system. Therefore, a capsule, such as the capsule 24 of FIG. 1, can also be relied upon to compress the waist of the stent frame during delivery. In this illustrated embodiment, the intermediate tension member 620b is wrapped around the release pin 70, stent frame and is connected to the second ring 664b via a knot 652b or otherwise for securing the tension member 620b through the second ring 664b.

Figure 11:
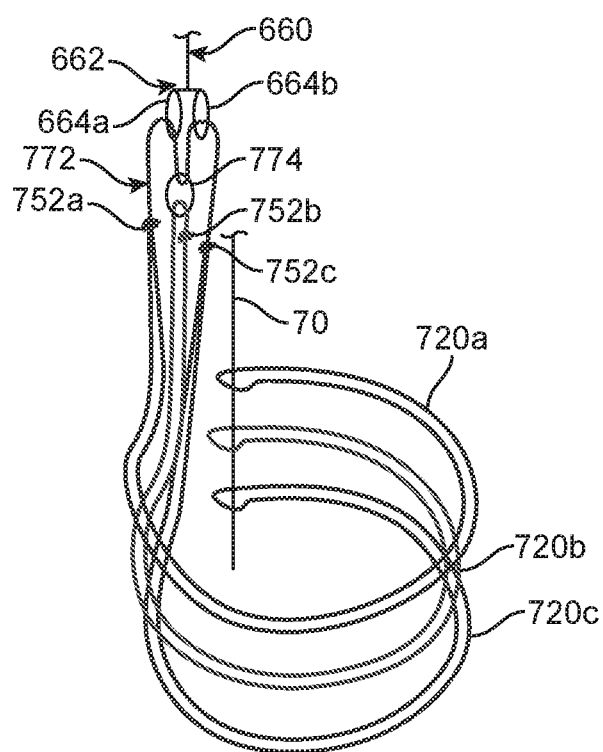
FIG. 11 is a schematic illustration of a way in which three elongate tension members can be releasably retained around a stented prosthesis (the stented prosthesis is not shown for ease of illustration).

Referring now also to FIG. 11, which illustrates an alternate configuration in which three elongate tension members 720a-c are provided. Outflow and inflow tension members 720a, 720c are threaded around a stent frame of a stented prosthesis (not shown for ease of illustration) and wrapped around the release pin 70. Respective ends 752a-b of the outflow and inflow tension members 720a, 720c are tied or otherwise connected to opposing ends of an interconnecting member 754, which can be considered a portion of the tension members 720a, 720c. The interconnecting member 772 can be made of the same material as the tension members 720a-c or a different material. In this embodiment, the interconnecting member 772 is slidably threaded through both rings 664a-b of the balancing element or connector 662. If the tension in the outflow and inflow tension members 720a, 720c becomes uneven, the interconnecting member 772 will naturally slide within the rings 664a-b to balance the tension in the two respective tension members 720a, 720c. If desired, the third, intermediate tension member 720b is routed through a third balancing element 774, around the stent frame, to and around the release pin 70 and then ends 752c of the intermediate tension member 720b are tied together or otherwise connected so that the intermediate tension member 720b forms a loop. In this embodiment, the balancing element 774 is a ring and further interconnects the interconnecting member 772 and the intermediate tension member 720b so that all three tension members 720a-c are interconnected and can slide and balance tension with respect to one another. As with prior disclosed embodiments, proximal and distal movement of the actuator 760 correspondingly tensions and releases tension in the intermediate tension member 720b uniformly with the outflow and inflow tension members 720a, 720c. In this embodiment, all three of the rings 664a, 664b and 774 allow the tension members 720a-c to adjust and slide with respect to each other, thus balancing the tension in each tension member 720a-c.

Figure 12:
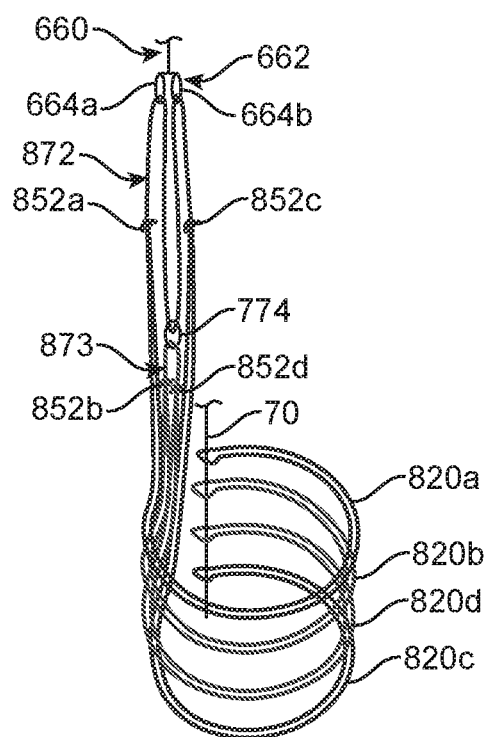
FIG. 12 is a schematic illustration of a way in which four elongate tension members can be releasably retained around a stented prosthesis (the stented prosthesis is not shown for ease of illustration).

Turning now also to FIG. 12, which illustrates a similar configuration as compared to that of FIG. 11 but which includes four tension members 820a-d. In this embodiment, outflow and inflow tension members 820a, 820c that can be routed around the stent frame (not shown for ease of illustration) and wrapped around the release pin 70. Respective ends 852a, 852c of the outflow and inflow tension members 820a, 820c are tied or otherwise connected to opposing ends of an interconnecting member 774. The interconnecting member 774 can be considered a portion of the tension members 820a, 820c and can be made of the same material as the tension members 820a-d or a different material. The interconnecting member 774 is slidably threaded through rings 664a-b of the connector 662. If the tension in the outflow and inflow tension members 820a, 820c becomes uneven, the interconnecting member 774 will naturally slide within the rings 864a-b to balance the tension in the two respective tension members 820a, 820c. The third and fourth, intermediate tension members 820b, 820d are wrapped from through a balancing ring 774, around the stent frame, to and around the release pin 70 and then ends 852b, 852d of the intermediate tension members 820b, 820d are tied together or otherwise connected so that the intermediate tension member 820b, 820d form respective loops. In this embodiment, the additional balancing ring 774 is provided spaced between the first and second rings 664a, 664b and interconnects the interconnecting member and the intermediate tension members 820b, 820d. As with prior disclosed embodiments, proximal and distal movement of the actuator 660 correspondingly tensions and releases tension in the intermediate tension members 820b, 820d uniformly with the outflow and inflow tension members 820a, 820c. In this embodiment, all three of the rings 664a, 664b and 774 allow the tension members 820a-d to adjust and slide with respect to each other, thus balancing the tension in each tension member 820a-d.

Figure 13A:
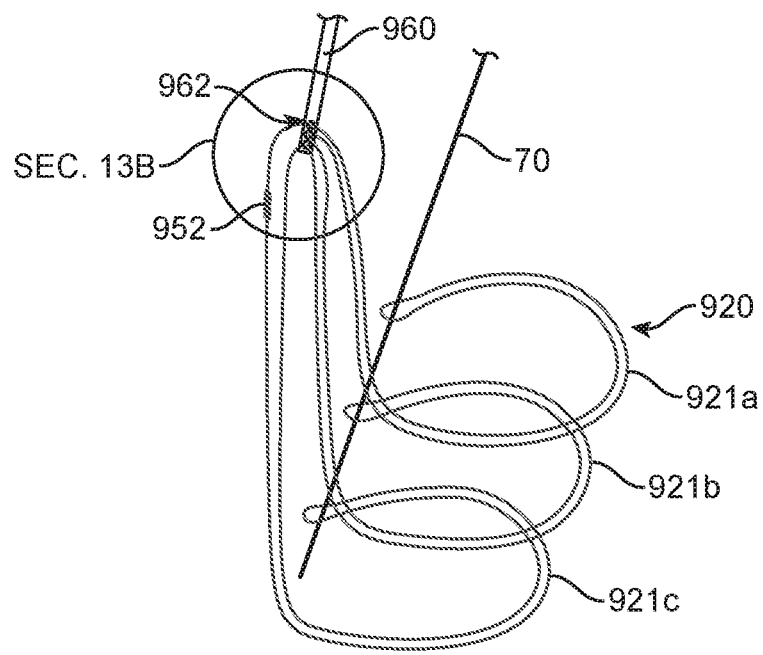
FIG. 13A is a schematic illustration of yet another way in which a plurality of elongate tension members are releasably positioned around a stented prosthesis with a release pin and tension in the tension members is balanced with a balancing element (the stented prosthesis is not shown for ease of illustration).
Figure 13B:
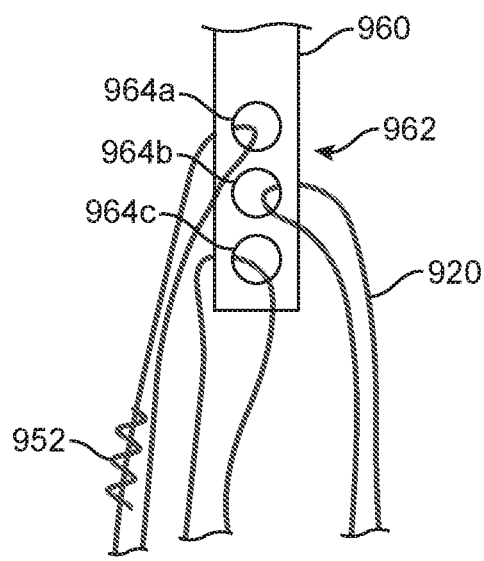
FIG. 13B is an enlarged schematic illustration of Sec. 13B of FIG. 13A illustrating the connection between the tension members and the balancing element.

Turning now also to the embodiment of FIGS. 13A-13B, which illustrate a configuration similar to that of FIG. 4. In this embodiment, an actuator 960 includes a balancing element 962 including three rings 964a-c arranged longitudinally along a length of the actuator 960. The rings 964a-c can be three linearly positioned, rigid openings in the actuator 960, for example. In this configuration, a single elongate tension member 920 is slidably threaded through each of the rings 964a-c and around the release pin 70 to change directions as the tension member 920 wraps around the inflow, waist and outflow ends of a stent frame of a stented prosthesis (not shown for ease of illustration). The tension member 920 therefore wraps around the release pin 70 three times to change direction as the tension member 920 forms three loops 921a-c having a double thickness of material around the stent frame. Two ends of the elongate tension member 920 can be connected with a knot 952 or the like.

Figure 14:
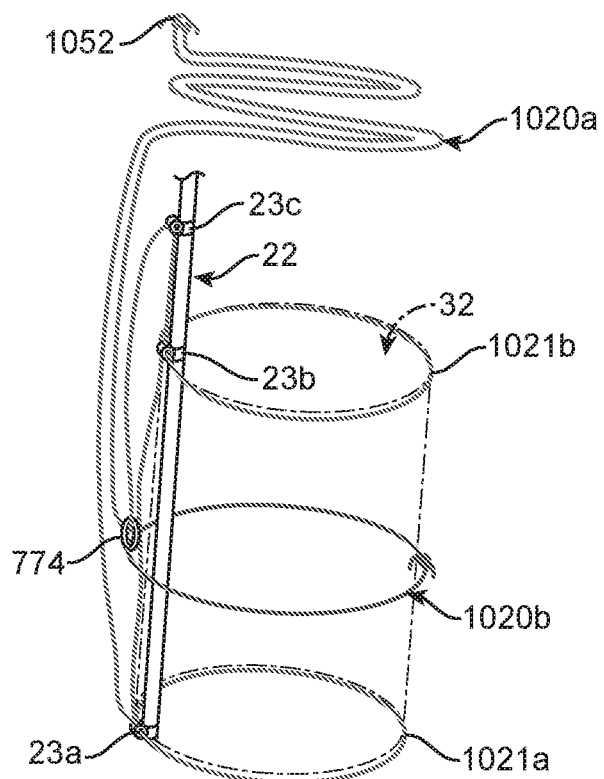
FIG. 14 is a schematic illustration of one way in which two elongate tension members can be positioned around a stent frame (shown schematically in phantom).

Now also referring to FIG. 14, which illustrates an alternate way in which two elongate tension members 1020a-b can be secured around a stent frame to jointly actuate each of the tension members. FIG. 14 shows the distal portion 22 of a delivery device, such as that of FIG. 1. The distal portion 22 includes a plurality of guides 23a-c positioned along a length of the distal portion 22. The first tension member 1020a extends over the first guide 23a and then around the stent frame 32 (shown schematically in phantom) to form a first loop 1021a. The first tension member 1020a then extends proximally to and is wound over the second guide 23b and then around the stent frame 32 to form a second loop 1021b. The tension member 1020a then extends distally to and through a balancing element 774, such as that disclosed above, and then extends proximally to the first end of the tension member 1020a so that the ends 1052 of the tension member 1020a can be tied or otherwise joined, as illustrated. The second tension member 1020b extends around the waist of the stent frame 32 and through the balancing element 774. The distal portion 22 can function as an actuator and is arranged and configured to be proximally retracted to tension the first and second tension members 1020a-b. Each of the tension members 1020a-b can slide within the balancing element 774 to equalize the tension applied by the actuator (i.e. distal portion 22). This embodiment does not include a release pin as discussed with respect to other embodiments. Once the stent frame 32 or other stented prosthesis is deployed, the first tension member 1020a is severed proximate or at the delivery device handle assembly to release the delivery device from the stent frame 32. In this embodiment, the second tension member 1020b is left within the patient along with the stent frame 32.

Figure 15:
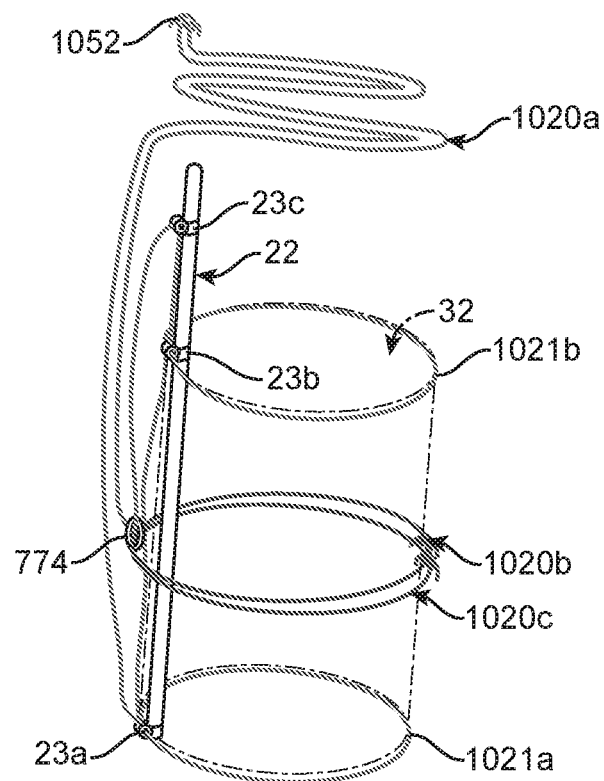
FIG. 15 is a schematic illustration of a way in which three elongate tension members can be positioned around the stent frame (shown schematically in phantom).

Turning now also to FIG. 15, which illustrates a configuration substantially similar to that of FIG. 14 but including two waist tension members 1020b-c. In this embodiment, each of the waist tension members 1020b-c are secured through the balancing ring 774 and remain in the patient, around the stent frame 32, after withdrawal of the delivery device.

Figure 16:
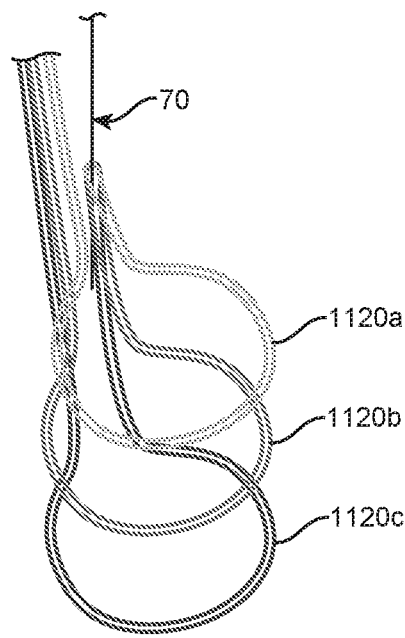
FIG. 16 is a schematic illustration of a way in which three elongate tension members can be positioned around a stented prosthesis (the stented prosthesis is not shown for ease of illustration).

Now referring additionally to FIG. 16, which illustrates three elongate tension members 1120a-c, which can be tensioned independently and individually by a plurality of respective actuation and release assemblies (not shown; actuation and release assemblies can be positioned within a quick connect or a handle assembly, such as the handle assembly of FIG. 1). In this embodiment, each elongate tension member 1120a-c extends from the respective actuation and release assembly (not shown), through independent lumens in a shaft assembly (e.g., the shaft assembly 16 of FIG. 1), around the stent frame (not shown for ease of illustration) and then around the release pin 70. Then the respective tension member 1120a-c wraps back around the stent frame and to its actuation and release assembly of the handle assembly. To release the tension members 1120a-c from the stent frame, the release pin is proximally retracted to disengage from the tension members 1120a-c and one end of each of the tension members 1120a-c is released so that the other ends of the tension members 1120a-c can be proximally retracted a sufficient amount to withdraw the full length of the tension members 1120a-c from the patient.

Figure 17:
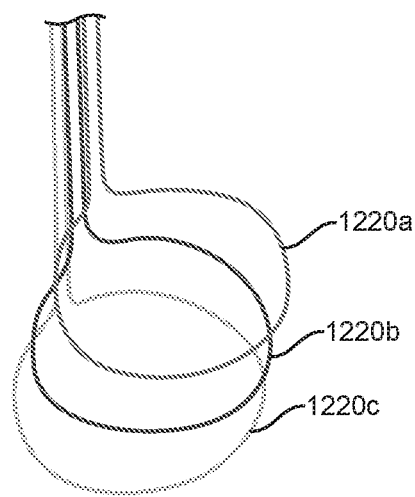
FIG. 17 is a schematic illustration of a way in which three elongate tension members can be positioned around a stented prosthesis (the stented prosthesis is not shown for ease of illustration).

Now additionally referring to FIG. 17, which illustrates a configuration having three elongate tension members 1220a-c that are not connected to a release pin as disclosed with respect to prior embodiments. In this embodiment, each tension member 1220a-c extends from a handle assembly or the like (see, e.g., the handle assembly 18 of FIG. 1), through respective lumens within a shaft assembly (e.g., the shaft assembly 16 of FIG. 1) and then wraps around the stent frame (not shown for ease of illustration) and then back to the handle assembly or the like. In this way, the three tension members 1220a-c define three loops around the stent frame. The handle assembly (not shown) can include an actuation and release assembly for each tension member 1220a-c that is configured to actuate tensioning adjustment and release of the respective tension member 1220a-c so that each tension member 1120a-c can be withdrawn from the stent frame after deployment of the stent frame. This embodiment is beneficial in that all tension members 1220a-c can be actuated uniformly and individually, to result in a symmetric crimping of the stent frame. Alternatively, the tension members 1220a-c can be tensioned to crimp the ends of the stent frame prior to crimping the waist, for example. In other words, tension members 1220a and 1220c can be selectively tensioned prior to or greater than the tension member 1220b. Since the tension members 1220a-c are controlled by individual actuation and release assemblies, control of the tension in each tension member is individually controlled. Once the stented prosthesis is deployed, one end of each of the tension members 1220a-c can be released so that the tension members 1220a-c can be withdrawn and unwrapped from the stented prosthesis for removal from the patient.

Figure 18:
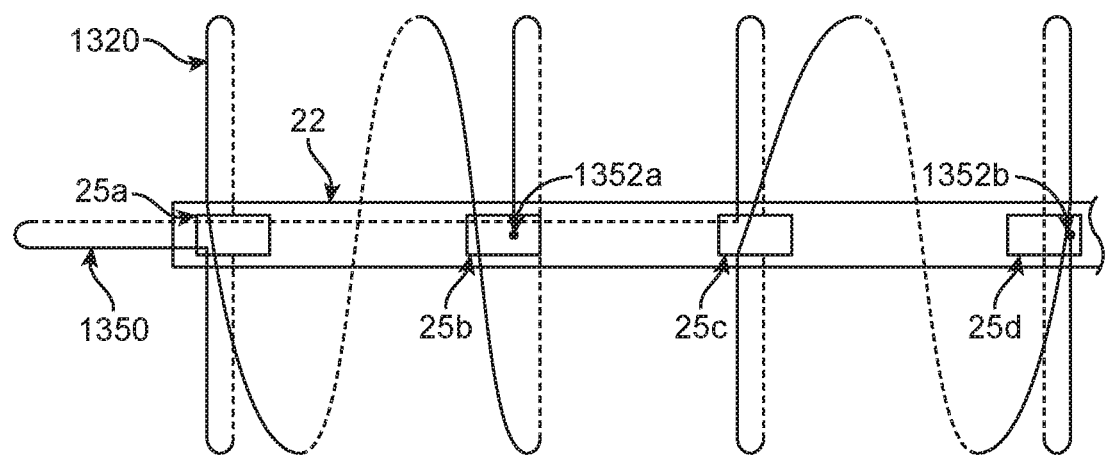
FIGS. 18-19 illustrate a way in which a single elongate tension member can be releasably positioned around a stented prosthesis such that as the tension member is tensioned, ends of the stented prosthesis compress before a waist section of the stented prosthesis (the stented prosthesis is not shown for ease of illustration in FIG. 18, however, various portions of the elongate tension member are shown in phantom to illustrate dimension if the tension member was routed around a stented prosthesis).
Figure 19:
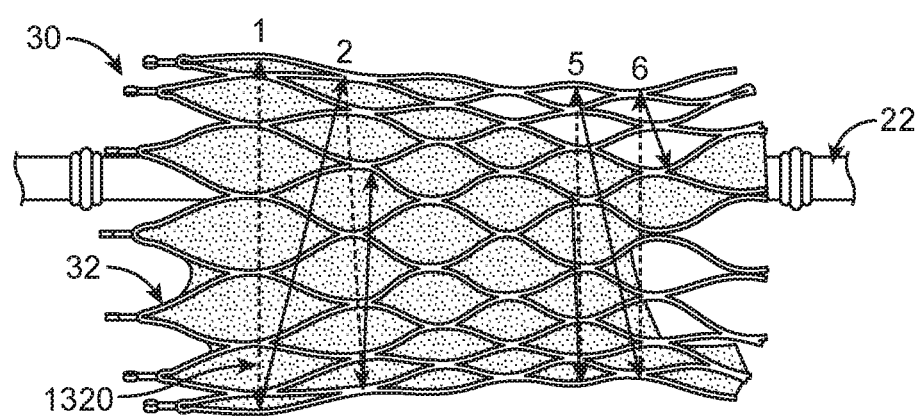

Referring now in addition to FIGS. 18-19, which collectively illustrate yet another configuration of how an elongate tension member 1320 can be routed and secured over the distal portion 22 and through windows 25a-d provided in the distal portion 22 to compressively secure a stented prosthesis, such as the stented prosthesis 30 (FIGS. 3A-3B) to the distal portion 22. The stented prosthesis is not shown in FIGS. 18-19, however, various portions of the elongate tension member 1320 are shown in phantom to illustrate dimension if the tension member 1320 was routed around a stented prosthesis. In this embodiment, the tension member 1320 is wound in a double helix pattern (generally from 1 to 2 to 3 to 4 to 5 to 6 and so on), one helix at one end of the distal portion 22 (and, thus one end of the stented prosthesis 30) and a second helix at a second end of the distal portion 22 (and, thus a second end of the stented prosthesis). At a proximal end of the distal portion 22, the tension member 1320 forms a loop 1350, which can be connected to and pulled or pushed by an actuator (not shown) to adjust tension in the tension member 1320 either by proximally retracting or distally advancing the actuator, respectively. In this embodiment, each end 1352a-b of the tension member 1320 includes a knot or the like (not shown), which anchors the tension member 1320 against a release pin (not shown) positioned within the distal portion 22. The release pin can be the release pin 70 disclosed with respect to other embodiments. In the disclosed embodiment, the anchor points at ends 1352a-b are located such that, when a tensioning force is applied to the tension member 1320 with the actuator, the inflow and outflow ends of the stent frame compress first, followed by compression of the waist upon further tensioning of the tension member 1320.

Figure 20:
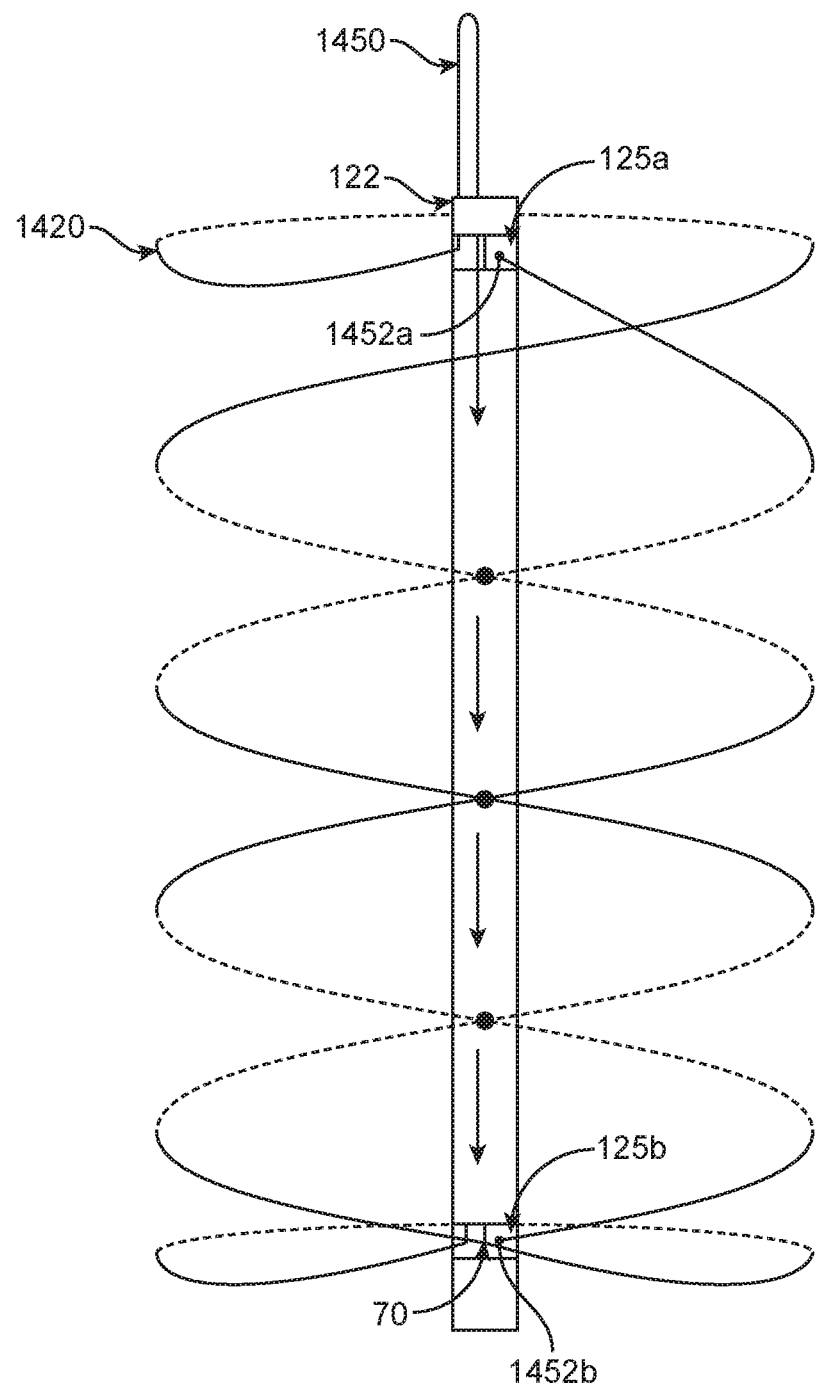
FIG. 20 is a schematic illustration of a way in which a single elongate tension member can be releasably positioned around a stented prosthesis such that as the tension member is tensioned, ends of the stented prosthesis compress gradually compressing the profile down at a waist of the stented prosthesis (the stented prosthesis is not shown for ease of illustration, however, various portions of the elongate tension member are shown in phantom to illustrate dimension if the tension member was routed around a stented prosthesis).

Now turning also to FIG. 20, which illustrates an additional configuration of how an elongate tension member 1420 can be secured over a distal portion 122 (which can be configured largely similar to the distal portion 22 disclosed above) and through apertures 125a-b in the distal portion 122 to compressively secure a stented prosthesis, such as the stented prosthesis 30 (FIGS. 3A-3B), to the distal portion 122. In this embodiment, the tension member 1420 is routed in a coiled configuration, as shown. The stented prosthesis is not shown in FIG. 20, however, various portions of the elongate tension member 1420 are shown in phantom to illustrate dimension if the tension member 1420 was routed around a stented prosthesis. This configuration can be described as include two coils that travel up and down a length of the stented prosthesis (not shown for ease of illustration). In this embodiment, one coil formed by the tension member 1420 begins at the proximal end of the stented prosthesis and travels in a coiled pattern distally and is tied off at a distal end of the distal portion. The second coil formed by the tension member 1420 begins at the distal end of the distal portion 122 and travels in a coiled pattern toward the proximal end of the distal portion 122 and is tied to the release pin proximate the proximal end of the distal portion. Each end 1452a, 1452b of the tension member 1420 includes a knot or is otherwise configured to be secured or anchored to the release pin 70 positioned within the distal portion, as with the prior disclosed embodiment (schematically illustrated). The tension member 1420 further provides a loop 1450 at a proximal end of the tension member 1420 that can be connected to an actuator (not shown) so that proximal retraction of the actuator translates into proximal retraction of the loop 1450, which correspondingly tensions the tension member 1420. As a tensioning force is applied to the loop 1450 by the actuator, the coils formed by the tension member 1420 begin to tighten at the ends of the stented prosthesis first and gradually compress the waist as further tension is applied by the actuator.

The balancing elements disclosed herein can take a variety of configurations. FIG. 21 illustrates one balancing element that is configured to be a ring 1574 that can be used in the embodiments of FIGS. 11-12 and 14-15, for example as a general equivalent of balancing element 774. For example, the ring 1574 can be positioned to interface between one or more tension members 1520 and an interconnecting member 1572 of any of the types disclosed above. This configuration resists binding of tension members 1520, which can occur when two tension members are directly connected. The ring 1574 can be made of a flattened coil or from joining two ends of a wire with welding, for example. Alternatively, the ring 1574 can be stamped and then edges could be coined and electropolished. The ring 1574 can be oval, oblong or kidney shaped, for example.

An actuator 1660 having an alternate balancing element 1662 is illustrated in FIG. 22. This actuator 1660 can be used in place of any actuator disclosed herein such as actuators 160, 360, 660, for example. In this embodiment, the balancing element 1662 includes two rings 1664a, 1664b (e.g., wire loops) on the end through which one or more tension members 1620 or interconnecting members 1674 can be threaded. The rings 1664a, 1664b can be made of wire having a smooth surface finish, which allows any tension member(s) 1620 and interconnecting members 1674 routed therethrough to easily slide and adjust within the respective rings 1164a, 1664b, which is beneficial for balancing tension in and between the tension member(s) 1620. The rings 1664a, 1664b can optionally include a coating, such as PTFE, to further improve the coefficient of friction. It will be understood in view of this disclosure that other balancing elements and rings of the disclosure can also benefit from such a coating.

Referring now also to FIGS. 23A-23C, which further illustrate an alternate actuator 1760 having a balancing element 1762, which includes slots 1764a, 1764b separated by a pin 1766 at a distal end of the actuator 1760. The pin 1766 has a smooth rounded surface and can optionally be rotatable within the connector 1762. One or more tension elements 1720a, 1720b (FIG. 23C) are connected to the actuator 1760 either directly or via an interconnecting member 1772 threaded through the slot and over the pin 1766. As shown in FIG. 23C, each elongate tension member 1720a, 1720b can be tied or otherwise connected to the interconnecting member 1772, with a knot 1752a, 1752b, for example. The interconnecting member 1772 can be considered part of the elongate tension members 1720a-b. The one or more tension elements 1720a, 1720b can slide within and with respect to the pin 1766, thus allowing tension and load applied by the actuator 1760 to naturally balance the tension in each tension element 1720a, 1720b. In some embodiments, the slots 1764a, 1764b are sized and the pin 1766 is positioned such that the knots 1752a, 1752b of each respective tension and interconnecting member cannot travel past the pin 1766.

Figure 24:
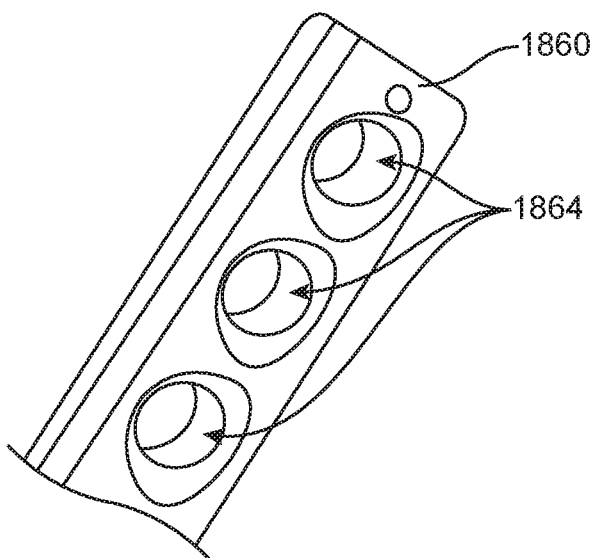
FIG. 24 is a partial, perspective view of yet another balancing element that can be used with the embodiments disclosed herein.

Turning now also to FIG. 24, which illustrates a distal end of an alternate actuator 1860 including a plurality of apertures 1864 (only a few of which are referenced) having beveled, rounded or otherwise smoothed edges through which tensioning elements or interconnecting members disclosed above can be threaded, similar to how the tension member 1720a-b or interconnecting member 1772 is retained within the slots 1764a, 1764b of FIGS. 23A-23C. As shown, the apertures in this embodiment are linearly spaced within the same plane. The apertures 1864 may be machined or otherwise formed. The apertures 1864 allow the tensioning members, such as those disclosed herein, to be uniformly actuated and tensioned and further allows the tension members to naturally slide within the apertures 1864 and adjust so that the tension in each of the tension members is equally distributed or balanced.

Figure 25:
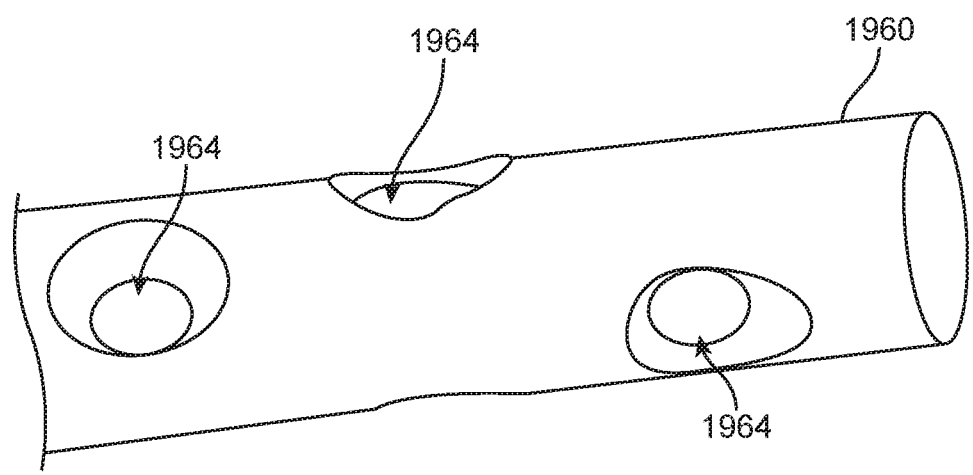
FIG. 25 is a partial, perspective view of a further balancing element that can be used with the embodiments disclosed herein.

Referring now also to FIG. 25, which illustrates a distal end of an alternate actuator 1960 including a plurality of offset apertures 1964 having beveled, rounded or otherwise smoothed edges through which tensioning members or interconnecting members, disclosed above, can be threaded. By offsetting the apertures 1964, the tension members of the type disclosed herein (not shown in FIG. 25) can be spaced so that they do not contact one another, which minimizes the required lumen size of the overall system. The three apertures 1964 can be offset by 120 degrees, when there are three tension members, for example. Alternate configurations including more or fewer apertures and tension members are envisioned.

Figure 26:
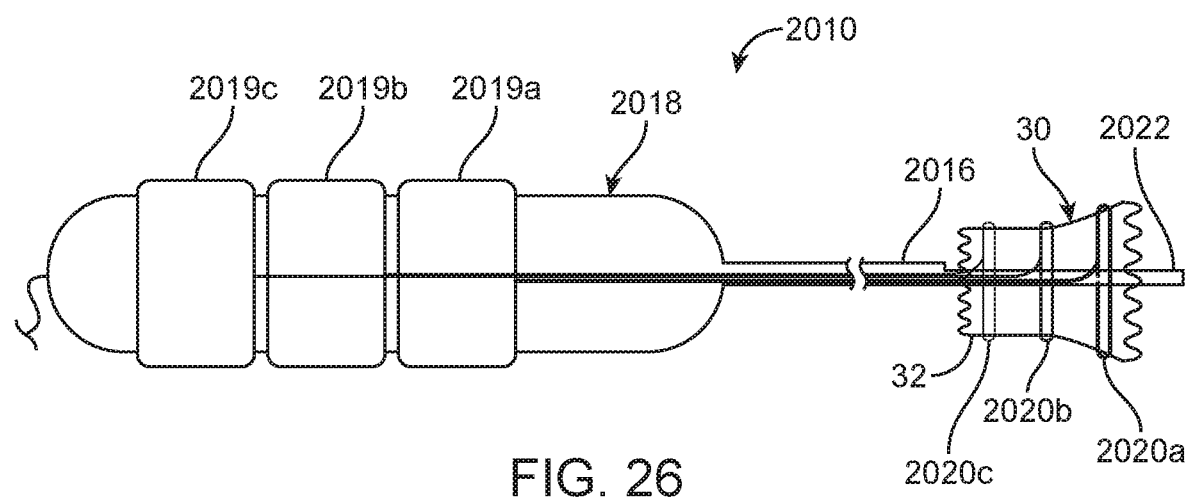
FIG. 26 is a schematic illustration of an alternate delivery device having a plurality of actuators to control a plurality of elongate tension members.
Figure 27A:
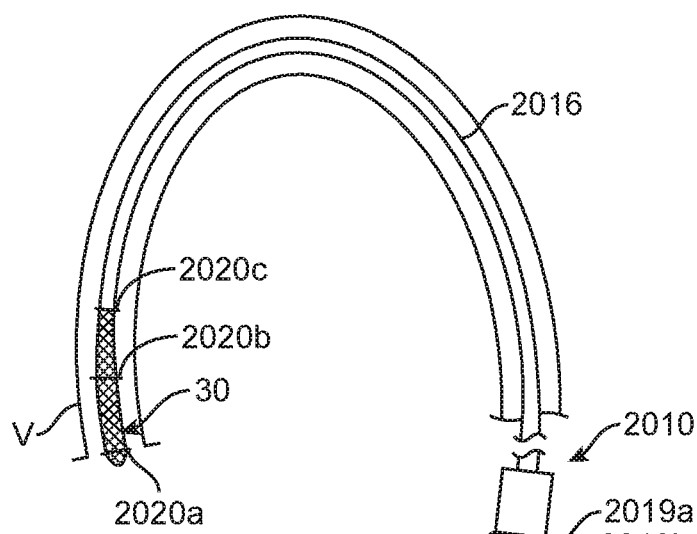
FIGS. 27A-27C are schematic illustrations of the delivery device of FIG. 26 being used to deliver and implant the stented prosthesis of FIGS. 3A-3B to a valve.
Figure 27B:
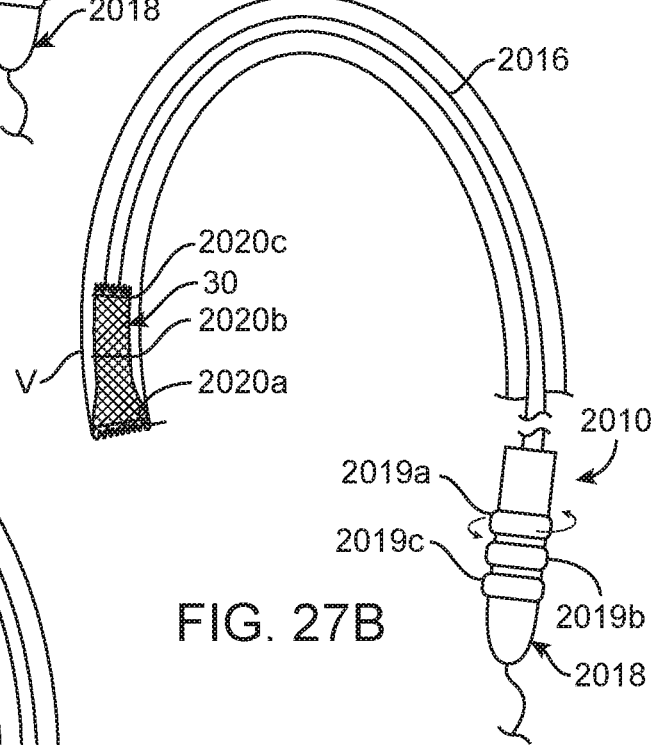
Figure 27C:
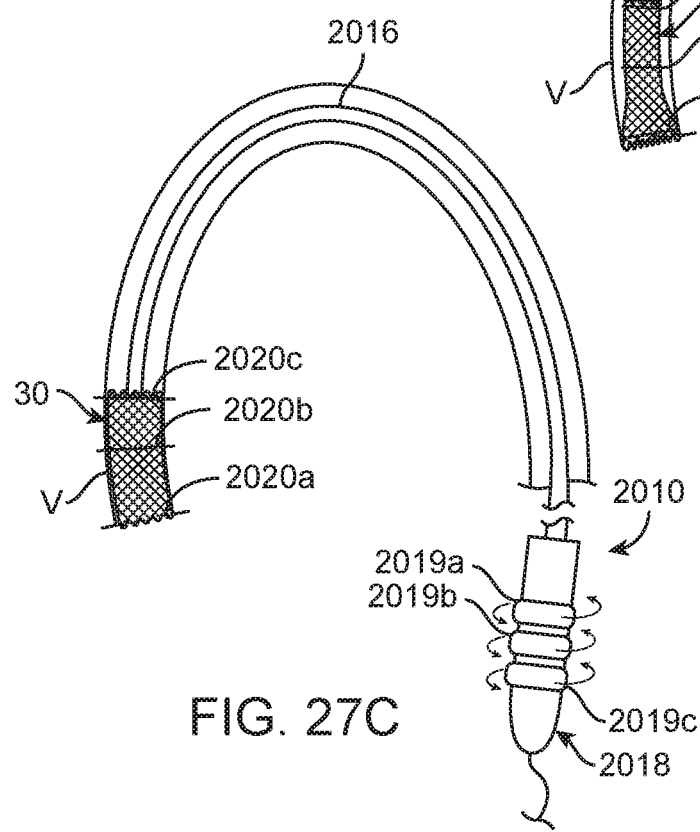

Turning now also to FIGS. 26-27C, which schematically illustrate an alternate delivery device 2010 configured for optional staggered adjustment of tension within a plurality of elongate tension members 2020a-c compressively retaining a stented prosthesis 30 to a spindle 2022 of the delivery device 2010. The delivery device 2010 can operate and be configured similar to the delivery device 10 of FIGS. 1-2B in all ways except as expressly stated. In this illustrative embodiment, three elongate tension members 2020a-c are provided and configured, for example, as shown in FIG. 17, however, more or fewer elongate tension members are envisioned. Each elongate tension member 2020a-c extends from the stented prosthesis 30 within or along a shaft assembly 2016 to a handle assembly 18. The handle assembly 2018 includes three actuation and release assemblies 2019a-c, one interconnected to each elongate tension member 2020a-c. In this way, a clinician can control each elongate tension member 2020a-c individually. In an alternative embodiment, three elongate tension members may be provided and configured, for example, as shown in FIG. 16, wherein the three elongate tension members are interconnected to three actuation assemblies and to a release pin. In this embodiment, a clinician can control the tension of each elongate tension member individually but release the three elongate tension members together via a release pin. The stent frame 32 of the prosthesis 30 can be compressed in sections (distal, waist, proximal) to minimize compression force in the shaft assembly 2016 to allow for a more flexible shaft construction. In addition, individual elongate tension member 2020a-c control allows the clinician to anchor the stented prosthesis 30 proximally or distally first by rotating the actuator corresponding to the proximal or distal tension member in order to release the proximal or distal section of the prosthesis first. It will be understood that the number of tension members can vary and, correspondingly, the number of actuation and release assemblies can also vary, as desired.

One example procedure is conducted as follows. The stented prosthesis 30 is loaded and compressed onto the spindle 2022 of the delivery device 2010. Then, the stented prosthesis 30 is delivered via transcatheter procedure to a native valve V (FIG. 27A). The clinician can release the stented prosthesis 30 by rotating the three actuation and release assemblies 2019a-c until the stented prosthesis 30 is approximately 75% open (expanded) and the valve structure (not visible) functions. Then, tension in the distalmost elongate tension member 2020a is completely released via actuation and release assembly 2019a to lightly anchor the stented prosthesis 30 within the native valve V (FIG. 27B).

The clinician can then optionally pull or push the delivery device 2010 to cant, tilt, or pitch the stented prosthesis 30 co-axially. Once the stented prosthesis 30 is positioned, as desired, the clinician releases all tension in the remaining elongate tension members 2020*b-c* via actuation and release assemblies 2019*b-c*, respectively, to allow the stented prosthesis to fully expand (FIG. 27C). If recapture is desired, the clinician, via the appropriate actuation and release assembly 2019*a-c*, applies tension to the respective elongate tension member 2020*a-c* to compress the stented prosthesis 30 in stages where elongate tension force is high to minimize shaft assembly 2016 compression and movement. In situations where the elongate tension member force is low, all elongate tension members 2020*a-c* can be tensioned at the same time via the actuation and release assemblies 2019*a-c*.

The device of FIGS. 26-27C can also be configured to tension the elongate tension members 2020*a-c* individually and also release the elongate tension members 2020*a-c* individually via single actuation and release assembly (e.g., actuation and release assembly 2019*a*). In such an embodiment, the actuator (e.g., 2019*a*) could be configured to move one elongate tension member 2020*a* a predetermined distance, stop, and move on in sequence to the next elongate tension member 2019*b* and continue in sequence.

The embodiment of FIGS. 26-27C can optionally incorporate the balancing elements and other aspects of the previously disclosed embodiments to balance tension in the elongate tension members 2020*a-c*. Such balancing elements may be particularly useful in embodiments where multiple elongate tension members are controlled by a single actuation and release assembly. For example, in an alternative embodiment (not shown), the delivery device may include two actuator and release assemblies wherein one actuator is interconnected to one elongate tension member, e.g., a distal elongate tension member, while the other actuator is interconnected to a pair of balanced elongate tension members, e.g., a waist elongate tension member and a proximal elongate tension member. The waist elongate tension member and the proximal elongate tension member can be balanced as previously disclosed. In this embodiment, the clinician can release the stented prosthesis by rotating the two actuation and release assemblies until the stented prosthesis is approximately 75% open (expanded) and the valve structure functions. Then, tension in the distal elongate tension member is completely released to lightly anchor the stented prosthesis within the native valve. The clinician can then optionally pull or push the delivery device to cant, tilt, or pitch the stented prosthesis co-axially. Once the stented prosthesis is positioned, as desired, the clinician releases all tension in the remaining two elongate tension members via a single actuation and release assembly to allow the stented prosthesis to fully expand.

Although the present disclosure has been described with reference to preferred embodiments, workers skilled in the art will recognize that changes can be made in form and detail without departing from the spirit and scope of the present disclosure.

What is claimed is:

1. A method of deploying a stented prosthesis; the method comprising the steps of:
    delivering the stented prosthesis to a target site while the stented prosthesis is maintained in a collapsed orientation on a distal portion of a shaft assembly with a compression device comprising:
        a connector comprising a first aperture;
        a first tension member comprising a first end portion forming a first tension loop encircling the stented prosthesis, a second end portion forming a second tension loop encircling the stented prosthesis, and an intermediate segment between the first end portion and the second end portion that is slidably disposed within the first aperture of the connector to balance a tension between the first tension loop and the second tension loop, wherein a tension in the first tension loop and a tension in the second tension loop facilitate maintenance of the stented prosthesis in the collapsed orientation; and
        a third tension loop formed by the first end portion that encircles the stented prosthesis, wherein slidably disposing the intermediate segment within the first aperture further balances a tension between the first tension loop, the second tension loop, and the third tension loop; and
    moving the connector to adjust the tension in the first tension loop and the tension in the second tension loop while the intermediate segment is free to slide within the first aperture to balance the tension between the first tension loop and the second tension loop.

2. The method of claim 1, wherein a release pin releasably engages a first end of the first end portion of the first tension member and releasably engages a second end of the second end portion of the first tension member to facilitate maintenance of the stented prosthesis in the collapsed orientation, the method further comprising releasing the tension in the first tension loop and the tension in the second tension loop by disengaging the release pin from at least one of the first end and the second end of the first tension member.

3. A method of deploying a stented prosthesis; the method comprising the steps of:
    delivering the stented prosthesis to a target site while the stented prosthesis is maintained in a collapsed orientation on a distal portion of a shaft assembly with a compression device comprising:
        a connector comprising a first aperture and a second aperture;
        a first tension member comprising a first end portion forming a first tension loop encircling the stented prosthesis, a second end portion forming a second tension loop encircling the stented prosthesis, and an intermediate segment between the first end portion and the second end portion that is slidably disposed within the first aperture of the connector to balance a tension between the first tension loop and the second tension loop, wherein a tension in the first tension loop and a tension in the second tension loop facilitate maintenance of the stented prosthesis in the collapsed orientation;
        a balancing ring, wherein the intermediate segment of the first tension member is further slidably disposed within the second aperture and slidably disposed within the balancing ring between the first aperture and the second aperture; and
        a second tension member comprising a first end portion attached to the balancing ring and second end portion forming a third tension loop encircling the stented prosthesis, wherein moving the connector further adjusts a tension in the third tension loop; and
    moving the connector to adjust the tension in the first tension loop and the tension in the second tension loop while the intermediate segment is free to slide within the first aperture to balance the tension between the first tension loop and the second tension loop.

4. The method of claim 3, wherein a release pin releasably engages a first end of the first end portion of the first tension member, releasably engages a second end of the second end portion of the first tension member, and releasably engages a second end of the second end portion of the second tension member to facilitate maintenance of the stented prosthesis in the collapsed orientation, the method further comprising releasing the tension in the first tension loop and the tension in the second tension loop by disengaging the release pin from at least one of the first end and the second end of the first tension member.

5. A method of deploying a stented prosthesis; the method comprising the steps of:

delivering the stented prosthesis to a target site while the stented prosthesis is maintained in a collapsed orientation on a distal portion of a shaft assembly with a compression device comprising:

a connector comprising a first aperture and a second aperture;

a first tension member comprising a first end portion forming a first tension loop encircling the stented prosthesis, a second end portion forming a second tension loop encircling the stented prosthesis, and an intermediate segment between the first end portion and the second end portion that is slidably disposed within the first aperture of the connector to balance a tension between the first tension loop and the second tension loop, wherein a tension in the first tension loop and a tension in the second tension loop facilitate maintenance of the stented prosthesis in the collapsed orientation;

a balancing ring, wherein the intermediate segment of the first tension member is further slidably disposed within the second aperture and slidably disposed within the balancing ring between the first aperture and the second aperture; and a second tension member comprising a first end portion forming a third tension loop encircling the stented prosthesis, the second tension member comprising a second end portion forming a fourth tension loop encircling the stented prosthesis, and an intermediate segment of the second tension member between the first end portion of the second tension member and the second end portion of the second tension member is slidably disposed within the balancing ring to balance a tension between the third tension loop and the fourth tension loop, wherein moving the connector adjusts the tension in the first tension loop and the tension in the second tension loop while the intermediate segment of the first tension member is free to slide within the first aperture, the second aperture, and the balancing ring to balance the tension between the first tension loop and the second tension loop, and wherein the moving the connector further adjusts a tension in the third tension loop and a tension in the fourth tension loop while the intermediate segment of the second tension member is free to slide within the balancing ring to balance the tension between the third tension loop and the fourth tension loop; and moving the connector to adjust the tension in the first tension loop and the tension in the second tension loop while the intermediate segment of the first tension member is free to slide within the first aperture to balance the tension between the first tension loop and the second tension loop.

6. The method of claim 5, wherein a release pin releasably engages a first end of the first end portion of the first tension member, releasably engages a second end of the second end portion of the first tension member, releasably engages a first end of the first end portion of the second tension member, and releasably engages a second end of the second end portion of the second tension member to facilitate maintenance of the stented prosthesis in the collapsed orientation, the method further comprising releasing the tension in the first tension loop and the tension in the second tension loop by disengaging the release pin from at least one of the first end and the second end of the first tension member.

\* \* \* \* \*